(12) United States Patent
Chang

(10) Patent No.: US 7,718,040 B2
(45) Date of Patent: May 18, 2010

(54) PROPYLENE OXIDE RECOVERY PROCESS

(75) Inventor: Te Chang, West Chester, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 500 days.

(21) Appl. No.: 11/728,098

(22) Filed: Mar. 23, 2007

(65) Prior Publication Data

US 2008/0230369 A1 Sep. 25, 2008

(51) Int. Cl.
*B01D 3/40* (2006.01)
*C07D 301/32* (2006.01)

(52) U.S. Cl. .............................. 203/53; 203/55; 203/66; 549/541

(58) Field of Classification Search ................... 203/53, 203/55, 66; 549/541
See application file for complete search history.

(56) References Cited

U.S. PATENT DOCUMENTS

| | | | |
|---|---|---|---|
| 4,140,588 A * | 2/1979 | Schmidt ....................... 203/92 |
| 4,944,847 A * | 7/1990 | Snow ............................ 203/8 |
| 5,006,206 A * | 4/1991 | Shih et al. ..................... 203/55 |
| 5,464,505 A * | 11/1995 | Peters et al. .................. 203/64 |
| 6,024,840 A * | 2/2000 | Rueter .......................... 203/50 |
| 6,710,194 B1 | 3/2004 | Cochran et al. ............. 549/533 |
| 6,849,162 B2 * | 2/2005 | Teles et al. .................... 203/38 |
| 6,914,167 B2 | 7/2005 | Jubin et al. ................. 585/867 |
| 7,323,579 B2 * | 1/2008 | Gobbel et al. ............... 549/541 |
| 7,594,979 B2 * | 9/2009 | Patrascu et al. ................. 203/1 |
| 2007/0238888 A1 * | 10/2007 | Goebbel et al. ............. 549/541 |

FOREIGN PATENT DOCUMENTS

JP 4-352771 12/1992

* cited by examiner

*Primary Examiner*—Virginia Manoharan
(74) *Attorney, Agent, or Firm*—Kevin M. Carroll

(57) ABSTRACT

Product propylene oxide in a reaction mixture resulting from the reaction of propylene, oxygen and hydrogen or from the reaction of propylene and hydrogen peroxide is separated from propylene and/or propane by extractive distillation using methanol and/or water extractive distillation solvent.

8 Claims, 2 Drawing Sheets

PROPYLENE OXIDE RECOVERY PROCESS

BACKGROUND OF THE INVENTION

The present invention relates to the recovery of propylene oxide and especially to the separation of propylene and propane from a propylene oxide containing product/solvent stream such as from the reaction of propylene, oxygen and hydrogen or the reaction of propylene and hydrogen peroxide to form propylene oxide.

DESCRIPTION OF THE PRIOR ART

Processes are known for the production of propylene oxide by direct reaction of propylene, oxygen and hydrogen, or by reaction of propylene with hydrogen peroxide. See, for example, U.S. Pat. No. 6,710,194, Japan Kokai No. 4-352771, and many others.

In processes for the production of propylene oxide by direct reaction of hydrogen, oxygen and propylene over a catalyst such as Pd/TS-1 or by reaction of hydrogen peroxide with propylene over TS-1, it is necessary to remove soluble propylene and propane from the product/solvent stream before propylene oxide can be recovered. Conventionally, two depropanization distillation columns running at low and high pressures respectively, have been required to effectively separate propane and propylene from the product stream without significant loss of propylene oxide. The present invention provides a simplified and improved method for the propane and/or propylene separation.

SUMMARY OF THE INVENTION

In accordance with the present invention, an improved depropanization system is provided which does not require a high pressure depropanizer. Instead, a water and methanol stream, such as the process stream recovered as bottoms from crude propylene oxide distillation, is employed as an extractive distillation solvent in the low pressure extractive distillation depropanization operation thereby accomplishing substantially complete depropanization of the propylene oxide containing stream in a much simpler and effective manner. The method is particularly suitable for a direct PO process when high propylene concentration in the feed is not required.

DETAILED DESCRIPTION

Figure 1:
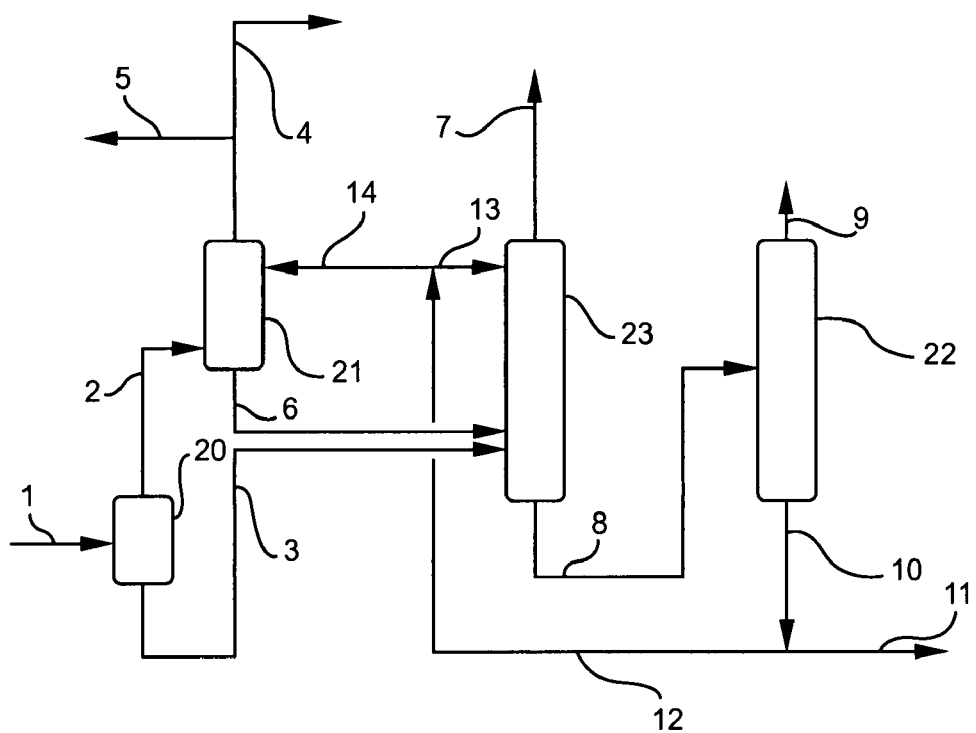
FIG. 1 illustrates schematically practice of the invention.

Referring to FIG. 1, a propylene oxide reaction product mixture stream comprised of propylene oxide, solvent, propylene, propane as well as various oxygenated materials is passed from a propylene oxide producing reaction unit (not shown) via line 1 to flash separator 20 wherein the mixture is flashed to form separate vapor and liquid phases. From separator 20 a vapor fraction is passed via line 2 to propylene oxide absorber 21 wherein propylene oxide is absorbed into an absorption methanol/water liquid comprised of a portion of the bottoms stream from the crude propylene oxide distillation column 22 which passes from column 22 via line 10, line 12 and line 14 to absorber 21. Overhead vapors from absorber 21 are recycled via line 5 to the propylene oxide reaction system with a small portion being sent via line 4 to a vent recovery system such as is described in U.S. Pat. No. 6,914,167. (not shown).

Liquid streams from flash separator 20 and propylene oxide absorber 21 are passed respectively via lines 3 and 6 to the lower section of low pressure depropanizer 23 along with a portion of the bottom stream from crude propylene oxide column 22 which passes to the upper section of depropanizer 23 and which serves as an extractive distillation solvent for the substantially complete separation of propylene and propane overhead from solvent which contains absorbed propylene oxide.

The solvent containing the absorbed propylene oxide passes from depropanizer 23 as bottoms via line 8 to crude propylene oxide column 22 wherein crude propylene oxide is distilled overhead via line 9 from a bottoms solvent stream most of which is recycled to the propylene oxide reactor via line 11 and part of which passes via lines 12 and 14 to the propylene oxide absorber 21 and via lines 12 and 13 to the low pressure depropanizer 23 for propylene oxide recovery as above described.

By this sequence substantially complete separation of propane and propylene from product propylene oxide is achieved by extractive distillation without the use of a high pressure depropanizer before separation of the propylene oxide from the reaction solvent. This results in substantial economics of separation.

Figure 2:
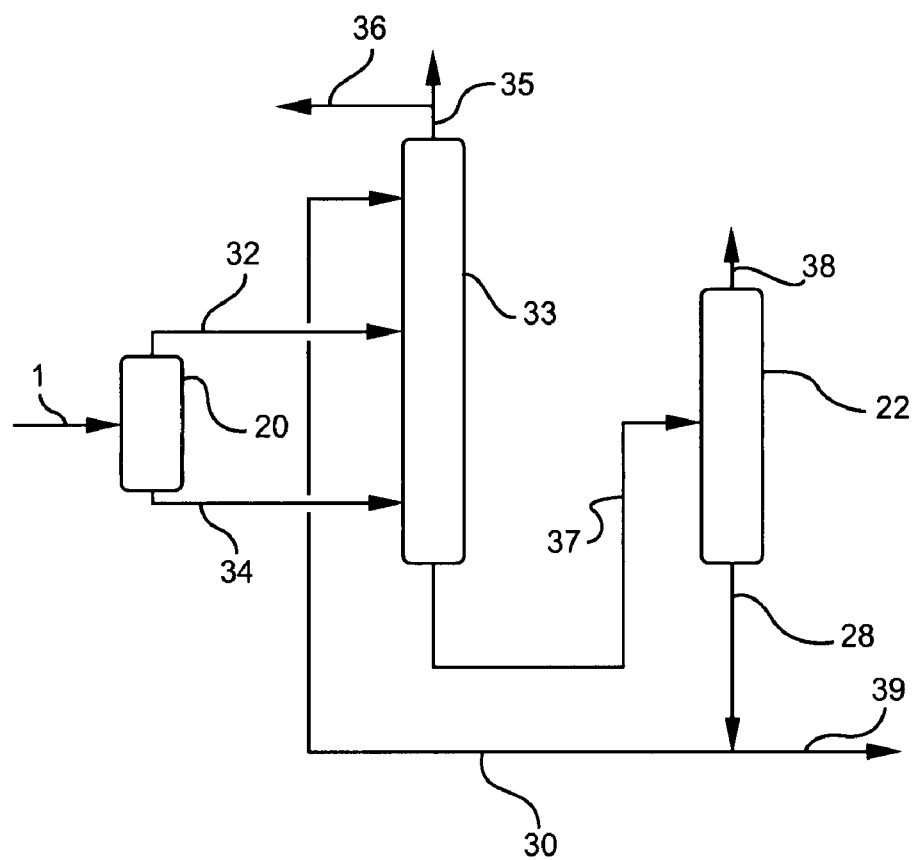
FIG. 2 illustrates schematically an especially advantageous embodiment of the invention.

A particularly preferred practice of the invention is described in accompanying FIG. 2. In this practice, both the propylene oxide absorption and the depropanization take place in a single extractive distillation column.

Referring to FIG. 2, a propylene oxide reaction product mixture stream passes via line 1 to flash separator 20. The mixture is flashed in separator 20 with the vapor stream passing via line 32 to the middle section of extractive distillation column 33. Liquid from the flash separator 20 is fed via line 34 to the bottom section of extractive distillation column 23. A recycle liquid solvent stream from crude propylene oxide column 22 is passed via lines 28 and 30 to the upper section of extractive distillation column 33 wherein it functions as extractive distillation solvent to separate propylene oxide from propylene and propane. The propylene and propane containing vapor stream passes overhead via line 35 with a portion going to a vent recovery system (not shown) and the remainder being recycled to the propylene oxide reaction system via line 36.

In extractive distillation column 33 the solvent absorbs propylene oxide into the solvent liquid and a liquid bottoms stream comprised of solvent and absorbed propylene oxide is removed from column 33 and passes via line 37 to the crude propylene oxide column 22 wherein product propylene oxide is separated overhead via line 38 and the bottoms liquid solvent stream is separated via lines 28 and 30 for recycle to column 33 with a portion being returned via line 39 to the propylene oxide reaction system.

This embodiment of the invention is especially advantageous in that both the propylene oxide absorption and the depropanization are readily accomplished in one extractive distillation column essentially using material indigenous to the system.

Generally speaking, the liquid reaction product mixture from the direct oxidation reaction comprises by weight about 1 to 6% propylene oxide, about 86 to 98% solvent and about 0.5 to 8% of propylene plus propane. The solvent mixture is generally a methanol/water mixture comprised by weight of 60 to 90% methanol and 10 to 40% water, and may contain 0 to 8% other materials, such as glycol ethers.

In practice of the invention, the liquid reaction product mixture from the propylene oxide producing reaction is fed to flash separator 20 in order to separate a lighter vapor phase stream from the heavier liquid solvent containing phase.

Propylene oxide is absorbed into solvent comprised of methanol and/or water in an extractive distillation step in either a separate absorber or in an integrated absorber/depropanizer thus separating the propylene oxide from non-absorbed propylene and/or propane components of the reaction mixture. The said solvent is preferably the methanol/water mixture used in the propylene oxide forming reaction such as is recovered as bottoms from crude propylene oxide distillation.

Example

Referring to FIG. 2, a reaction mixture from production of propylene oxide by reaction of propylene, oxygen and hydrogen is a slurry of Pd promoted TS-1 catalyst in a methanol-water solvent passes via line 1 to flash vessel 20 at the rate of 1000 lbs/hr. The reaction mixture is at 60° C. and 315 psia.

The mixture is flashed in vessel 20 with a vapor fraction being removed via line 32 at 40° C. and 125 psia at the rate of 325 lbs/hr. and a liquid fraction being removed via line 34 at 40° C. and 125 psia at the rate of 675 lbs/hr. The vapor fraction is comprised by weight of 1.1% propylene oxide, and 2.1% propane, 16.8% propylene and 80% others. The liquid fraction is comprised by weight of about 3.4% propylene oxide, about 0.7% propylene, about 0.1% propane, about 72% methanol and about 21% water.

The vapor fraction passes from flash vessel 20 via line 32 to absorber/depropanizer 33 and is introduced therein at an intermediate point while the liquid fraction is passed from flash vessel 20 via line 34 at the rate of 675 lbs/hr. to the lower section of absorber/depropanizer 33. Bottoms from crude propylene oxide column 22 is removed via line 28 with a portion recycled via line 39 to the propylene oxide forming reaction and a portion passing via line 30 to the upper section of absorber/depropanizer 33 at the rate of 350 lbs/hr. This bottoms stream comprises by weight about 73% methanol, about 22% water, and about 5% others. (including 2.75% PO).

In absorber/depropanizer 33, the stream passing from column 22 via line 30 functions as an extractive distillation solvent effective to separate the light hydrocarbon propane and propylene components overhead while retaining the propylene oxide which passes with the solvent from absorber/depropanizer 33 via line 37. It is possible to separate virtually all of the propane and propylene from the propylene oxide stream in this way as vapor thus enabling propylene oxide to be subsequently recovered in high purity.

In the operation shown in FIG. 2, absorber/depropanizer 33 is operated at relatively low pressure, the overhead stream being 27° C. and 35 psia and the bottoms being removed at 93° C. The overhead stream is removed at the rate of 82 lbs/hr. and comprises by weight 81% propylene and propane. The bottoms stream is removed at the rate of 918 lbs/hr. and comprises 2.8 wt. % propylene oxide.

In general, the extractive distillation solvent stream is used in amount of about 0.1 to 1 parts by weight per part of the combined streams fed via lines 32 and 34.

Although in the embodiment illustrated the methanol and water bottoms stream from column 22 is used for the extractive distillation, and this is the preferred practice, other sources of methanol and water can be provided to accomplish the extractive distillation.

In especially preferred practice, the extractive distillation is carried out at a pressure of 15 to 60 psia, preferably 15 to 40 psia, and the feed to the extractive distillation comprises a vapor stream containing not more than 80 wt. % propylene and propane, preferably not more than 30 wt. % propylene and propane and a liquid stream containing not more than 20 wt. % propylene and propane, preferably not more than 3 wt. % propylene and propane.

I claim:

1. In a process for the separation of propane and propylene from propylene oxide, produced by direct oxidation of propylene, the improvement which consists essentially of extractively distilling a feed comprising propylene oxide, methanol, water, propylene and propane in the presence of an extractive distillation solvent consisting essentially of methanol and water to separate an overhead stream comprising propylene and propane from a bottoms stream comprising propylene oxide, methanol and water.

2. The process of claim 1 wherein the extractive distillation solvent comprises the bottoms stream from a crude propylene oxide distillation.

3. The process of claim 1 wherein the feed to the extractive distillation comprises vapor and liquid from the direct oxidation of propylene.

4. The process of claim 1 wherein the feed to the extractive distillation comprises vapor and liquid from a reduced pressure flash of a reaction stream from the direct oxidation of propylene.

5. The process of claim 1 wherein the extractive distillation is carried out at a pressure of 15 to 60 psia.

6. The process of claim 1 wherein the extractive distillation is carried out at a pressure of 15 to 40 psia.

7. The process of claim 1 wherein the feed to the extractive distillation comprises a vapor stream containing by weight not more than 80% propylene and propane and a liquid stream containing by weight not more than 20% propylene and propane.

8. The process of claim 1 wherein the feed to the extractive distillation comprises a vapor stream containing by weight not more than 30% propylene and propane and a liquid stream containing by weight not more than 3% propylene and propane.

* * * * *